(12) United States Patent
Porter-Maloney et al.

(10) Patent No.: US 9,901,521 B2
(45) Date of Patent: Feb. 27, 2018

(54) WHITENING ORAL CARE COMPOSITIONS

(71) Applicant: COLGATE-PALMOLIVE COMPANY, New York, NY (US)

(72) Inventors: Venda Porter-Maloney, Piscataway, NJ (US); Suman K. Chopra, Monroe, NJ (US); Dennis Ontumi, Easton, PA (US)

(73) Assignee: Colgate-Palmolive Company, New York, NY (US)

( * ) Notice: Subject to any disclaimer, the term of this patent is extended or adjusted under 35 U.S.C. 154(b) by 24 days.

(21) Appl. No.: 15/106,920

(22) PCT Filed: Dec. 23, 2013

(86) PCT No.: PCT/US2013/077386
§ 371 (c)(1),
(2) Date: Jun. 21, 2016

(87) PCT Pub. No.: WO2015/099642
PCT Pub. Date: Jul. 2, 2015

(65) Prior Publication Data
US 2017/0027824 A1  Feb. 2, 2017

(51) Int. Cl.
*A61K 8/22* (2006.01)
*A61K 8/81* (2006.01)
*A61Q 11/02* (2006.01)
*A61K 8/49* (2006.01)
*A61Q 11/00* (2006.01)

(52) U.S. Cl.
CPC ............... *A61K 8/22* (2013.01); *A61K 8/492* (2013.01); *A61K 8/8176* (2013.01); *A61Q 11/00* (2013.01); *A61Q 11/02* (2013.01); *A61K 2800/43* (2013.01)

(58) Field of Classification Search
CPC .................................... A61K 8/22; A61K 8/81
USPC ..................... 424/10.3, 49, 53, 401
See application file for complete search history.

(56) References Cited

U.S. PATENT DOCUMENTS 9,174,070 B2    11/2015  Chopra et al.
2006/0045854 A1  3/2006  Zaidel et al.

FOREIGN PATENT DOCUMENTS

| CA | 2415783 | 7/2004 |
| EP | 1935395 A1 | 6/2008 |
| WO | WO 2013/095369 A2 | 6/2013 |

OTHER PUBLICATIONS

Corresponding International Search Report for PCT/US2013/077386.

*Primary Examiner* — Walter Webb

(57) ABSTRACT

Described herein are oral care compositions comprising a crosslinked polyvinylpyrrolidone complexed with hydrogen peroxide, together with a blue to violet-blue pigment; including some embodiments which further comprise an ethylene oxide, propylene oxide block co-polymer.

15 Claims, No Drawings

WHITENING ORAL CARE COMPOSITIONS

CROSS-REFERENCE TO RELATED PATENT APPLICATIONS

The present application is a U.S. national stage application under 35 U.S.C. §371 of PCT Application No. PCT/US2013/077386, filed Dec. 23, 2013, the entirety of which is incorporated herein by reference.

BACKGROUND

Many individuals are dissatisfied with their current tooth color. Thus, there is a desire for whiter teeth and one means to achieve whiter teeth is the use of tooth whitening products.

It is known in the literature that the visual perception of a white substance can be altered through the deposition of an optical brightener, blue pigment or blue dye, especially one for which the hue angle (in the CIELAB scale) of the reflected or emitted light is between 200 to 320 degrees. This effect is commonly used in laundry detergent products to make white clothes appear "whiter" to the human eye. The same concept has been applied to tooth whitening as well. The natural off-white or yellow color of teeth can be made to appear whiter through the deposition of a blue substance onto teeth. Using pigments with a deposition aid, i.e., high molecular weight Gantrez® type polymers (copolymers of maleic anhydride and with methyl vinylether) in toothpaste to make teeth look whiter is disclosed in EP 1935395B1.

Dentifrice formulations comprising peroxide are known and useful for cleaning and whitening teeth. The peroxide can bleach the teeth, remove stains, and kill cariogenic bacteria. However, peroxide compounds are highly reactive, and consequently difficult to formulate. Moreover, hydrogen peroxide can spontaneously decompose to form oxygen gas ($O_2$) and water, so that on storage, the dentifrice containers may bloat, burst or leak, and the remaining formulation will not have enough peroxide remaining to clean and whiten teeth effectively. Some dentifrices initially comprise very high levels of peroxide, which decomposes over time, so that the exact amount of peroxide delivered on application is variable and largely depends on how long and under what conditions the dentifrice has been stored.

Due to the color bleaching property of hydrogen peroxide, products containing hydrogen peroxide are usually clear or off white.

There is thus a need for improved color stable whitening oral compositions which effectively stabilizes both hydrogen peroxide and pigment that are suitable for everyday consumer use.

BRIEF SUMMARY

In some embodiments, the present invention provides oral care compositions that are stable during long term storage and remain effective to clean and whiten teeth. In some embodiments, the invention provides an oral care composition comprising: (i) a crosslinked polyvinylpyrrolidone complexed with hydrogen peroxide ("PVP-$H_2O_2$") and (ii) a pigment having a blue to blue-violet color with a hue angle in the CIELAB system ranging from 200 to 320 degrees.

In other embodiments, the invention provides an oral care composition comprising (i) a crosslinked polyvinylpyrrolidone complexed with hydrogen peroxide, and (ii) a pigment having a blue to blue-violet color with a hue angle in the CIELAB system ranging from 200 to 320 degrees, and (iii) an ethylene oxide, propylene oxide block co-polymer of formula (ethylene oxide$_x$-(propylene oxide)$_y$, wherein x is an integer of 80-150 and y is an integer 30-80, having an average molecular weight of greater than 5000 Da.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The term "wt %" is an abbreviation for weight percent. The amounts given are based on the active weight of the material.

In some embodiments the compositions of the invention further comprise an abrasive. In some embodiments, the abrasive is a calcium abrasive, in particular calcium pyrophosphate.

By exposure to aqueous environments, as in the oral cavity, the PVP-$H_2O_2$ dissociates into individual species (PVP polymer and $H_2O_2$). The PVP-$H_2O_2$ complex is generally comprised of about 80% by weight polyvinyl pyrrolidone and 20% by weight $H_2O_2$. Single phase whitening dentifrice compounds comprising PVP-$H_2O_2$ complexes are described, e.g., in WO/2007/037961, and its parent US Pub. No. US 2007-0071695 A1, the contents of which are incorporated herein by reference.

Peroxide is added to oral care compositions such as dentifrice, mouthrinses, strips, and gels to whiten teeth through the bleaching of stains. Peroxide removes color compounds by oxidation, in which the chemical bonds that make up the chromophore are broken and the molecule is changed into a different substance that does not contain the chromophore and does not absorb visible light. For this reason most oral care product containing peroxide are clear gels or off white. It has been surprisingly discovered that blue pigment color is not bleached by peroxide in the oral compositions of the invention. Thus, the present invention concerns a color stable formulation which effectively stabilizes both hydrogen peroxide and blue to blue-violet pigment.

Additionally, at a low concentration of peroxide, e.g., 0.01 to 4 wt %, in one embodiment 0.01 to 0.3 wt %, in another embodiment 0.1 to 0.3 wt %, in a dentifrice or mouthwash, it can be difficult for the low concentration of peroxide to provide instant whitening, i.e., whitening after only one use. The present invention achieves instant whitening at low levels of peroxide by combining with a blue to blue-violet pigment. Objects appear white because all colors are reflected back to the eye. The enamel is more transparent to blue light and so many stains absorb blue light. This reduces the whiteness of the enamel. Applying a blue to blue-violet color to the surface of teeth can mask yellow color by increasing the amount of blue or blue-violet light that is reflected back to the eye. Thus, blue to blue-violet color is capable of increasing the whitening perception of a tooth. Even white teeth can be made to appear whiter. The present invention provides a formulation which effectively delivers both hydrogen peroxide and blue to blue-violet pigment to provide an even higher superior whitening efficacy.

Accordingly, the invention provides a dentifrice comprising (i) a crosslinked polyvinylpyrrolidone complexed with hydrogen peroxide, (ii) a pigment having a blue to blue-violet color with a hue angle in the CIELAB system ranging from 200 to 320 degrees and, in one embodiment, (iii) an ethylene oxide, propylene oxide block co-polymer of formula (ethylene oxide)$_x$-(propylene oxide)$_y$ wherein x is an integer of 80-150, e.g. 100-130, e.g. about 118, and y is an integer 30-80, e.g. about 60-70, e.g. about 66, having an average molecular weight of greater than 5000, e.g., 8000-13000 Da, e.g. about 9800. In some embodiments the ethylene oxide, propylene oxide co-polymer is substantially free of an ethylene oxide, propylene oxide block co-polymer of average molecular weight less than 5000 Da. An example of a suitable commercially available ethylene oxide, propylene oxide co-polymer is PLURACARE® L1220 (available from BASF, Wyandotte, Mich., United States of America).

In some embodiments, the invention provides a toothpaste comprising an abrasive, e.g., a calcium abrasive. In other embodiments, the invention provides an abrasive-free gel.

For example, the invention provides Composition 1, an oral composition such as a dentifrice comprising (i) a whitening complex comprising crosslinked polyvinylpyrrolidone complexed with hydrogen peroxide, (ii) a pigment having a blue to blue-violet color with a hue angle in the CIELAB system ranging from 200 to 320 degrees, e.g.:

1.1 Composition 1 wherein said composition further comprises (iii) an ethylene oxide, propylene oxide block co-polymer of formula (ethylene oxide)$_x$-(propylene oxide)$_y$ wherein x is an integer of 80-150, e.g. 100-130, e.g. about 118, and y is an integer 30-80, e.g. about 60-70, e.g. about 66, having an average molecular weight of greater than 5000, e.g., 8000-13000 Da, e.g. about 9800, in an amount, e.g., of 0.01 to 15 wt, or 5 to 12 wt %, or about 7.5 wt %.

1.2 Composition 1 or 1.1 wherein the whitening complex contains about 10-30 wt %, e.g., 15-25 wt % for example about 17-22 wt % of hydrogen peroxide by weight, and about 5-15 wt %, for example about 7-12 wt % total nitrogen by weight; for example, having substantially the same specifications as Polyplasdone® XL-10, e.g., Polyplasdone® XL-10F, e.g., available from International Specialty Products (Wayne, N.J.);

1.3 Any of the foregoing compositions wherein the pigment has a hue angle in the CIELAB system ranging from 250 to 290 degrees;

1.4 Any of the foregoing compositions wherein the pigment is blue pigment such as Pigment Blue 2, 9, 10, 14, 15, 15:1, 15:2, 15:3, 15:4, 15:6 16, 18, 19, 24:1, 25, 56, 60, 61, 62 or 66, in particular Pigment Blue 15;

1.5 Any of the foregoing compositions further comprising a calcium abrasive wherein the calcium abrasive comprises a calcium phosphate salt, e.g., calcium pyrophosphate, dicalcium orthophosphate dihydrate, tricalcium phosphate, and calcium polymetaphosphate;

1.6 The immediately foregoing composition wherein the calcium abrasive comprises calcium pyrophosphate;

1.7 Composition 1.5 wherein the calcium abrasive comprises calcium carbonate;

1.8 Any of the foregoing compositions wherein the total amount of hydrogen peroxide by weight of the composition is 0.01 to 4%, or 0.01 to 3%, or 0.05 or 3%, or 0.075 to 2%, or 0.1 to 1.5%, or 0.01 to 0.3%, or 0.1 to 0.3%, or about 0.1%;

1.9 Any of the foregoing compositions wherein the amount of pigment by weight in the oral composition is 0.01 to 3%, or 0.02 to 1%, or 0.01 to 0.3%, or 0.02 to 0.3%, or 0.01 to 0.08%, e.g., about 0.075%;

1.10 Any of the foregoing compositions which contains less than 2 wt % water, e.g., less than 1 wt % water, e.g., is substantially anhydrous;

1.11 Any of the foregoing compositions comprising polymer thickeners selected from (i) polyethylene glycol, (ii) polyethylene glycol-polypropylene glycol block co-polymers having a molecular weight of at least 5000, and (iii) combinations thereof;

1.12 Any of the foregoing compositions additionally comprising polyethylene glycol of average molecular weight 400 to 800, e.g., about 600 Da;

1.13 Any of the foregoing compositions additionally comprising humectants, e.g. selected from glycerin, propylene glycol or a combination thereof;

1.14 Any of the foregoing compositions additionally comprising a tartar control agent, e.g., selected from tetrasodium pyrophosphate (TSPP) and sodium acid pyrophosphate (SAPP);

1.15 Any of the foregoing compositions additionally comprising a surfactant, e.g., sodium lauryl sulfate (SLS);

1.16 Any of the foregoing compositions additionally comprising an antibacterial agent, e.g., triclosan;

1.17 Any of the foregoing compositions additionally comprising an antioxidant, e.g., butylated hydroxytoluene (BHT);

1.18 Any of the foregoing compositions comprising any or all of the following ingredient classes and/or particular ingredients by weight:

| | |
|---|---|
| Humectants, e.g. Glycerin | 10-60%, or 20-50%, e.g., about 35% |
| Propylene glycol | 0.01-60%, or 5-25% e.g., about 15% |
| Thickeners, e.g., Fumed silica | 0-3%, e.g., about 1.75% |
| Polymers, e.g., Ethylene oxide, propylene oxide block co-polymer, avg. MW >5 kDa | 0.01-15%, or 5-12%, e.g., about 7.5% |
| Polyethylene glycol 600 | 0-15% or 1-15%, e.g., about 6% |
| additional linear and/or crosslinked polyvinylpyrrolidone | 0-10%, or 1-10%, or 0.25-10%, e.g., about 5.75% |
| Crosslinked polyvinylpyrrolidone complexed with 15-25% hydrogen peroxide | 0.05-25%, or 0.1-15%, or 0.25-10%, e.g., about 0.55% |
| Abrasive, e.g., Calcium pyrophosphate | 0.01-45%, or about 5-30%, e.g., about 20% |
| Fluoride, Sodium monofluorophosphate | 0-2% or about 0.1-1.5%, e.g. about 1.1% |
| Surfactant, e.g., SLS | 0-3%, or 0.1-3%, e.g., about 2% |
| Tartar control agent, e.g. TSPP and/or SAPP | 0.01-5%, or 0.1-4% e.g., about 2% |
| Antioxidant, e.g. BHT | 0.01-5%, e.g., about 0.03% |
| Flavorings | 0.1-5, e.g., 1.4% |
| Phosphoric acid | 0.01-3%, e.g., 0.2% |
| Pigment Blue, e.g., Pigment Blue 15 | 0.01-3%, or 0.02-1%, or 0.01-0.3%, or 0.01-0.08%, e.g., about 0.075% |
| Water | <3% |

1.19 The composition resulting from the combination of the preceding ingredients;

1.20 Any of the foregoing compositions in the form of a mouthwash or toothpaste.

In another embodiment, the invention provides a dentifrice comprising a crosslinked polyvinylpyrrolidone complexed with hydrogen peroxide, together with additional linear and/or crosslinked polyvinylpyrrolidone, and a dentifrice carrier.

In some embodiments, the present invention provides oral care compositions comprising: a crosslinked polyvinylpyrrolidone complexed with hydrogen peroxide, a blue to blue-violet pigment, a stabilizing amount of an additional linear and/or crosslinked polyvinylpyrrolidone, an abrasive and a humectant.

Some embodiments provide oral care compositions comprising: from about 0.05 to about 25%, by weight, crosslinked polyvinylpyrrolidone complexed with hydrogen peroxide. Other embodiments provide oral care compositions comprising: from about 0.1 to about 15%, by weight, crosslinked polyvinylpyrrolidone complexed with hydrogen peroxide. Still other embodiments provide oral care compositions comprising: from about 0.25 to about 10%, by weight, crosslinked polyvinylpyrrolidone complexed with hydrogen peroxide. Yet other embodiments provide oral care compositions comprising: from about 0.5 to about 10%, by weight, crosslinked polyvinylpyrrolidone complexed with hydrogen peroxide. While other embodiments provide oral care compositions comprising: from about 0.5 to about 8%, by weight, crosslinked polyvinylpyrrolidone complexed with hydrogen peroxide. In some embodiments, the oral care compositions comprise 0.5 to about 5%, by weight, crosslinked polyvinylpyrrolidone complexed with hydrogen peroxide, or about 0.5 to about 3%, by weight, crosslinked polyvinylpyrrolidone complexed with hydrogen peroxide, or about 0.5 to about 2%, by weight, crosslinked polyvinylpyrrolidone complexed with hydrogen peroxide, or about 0.55%, by weight, crosslinked polyvinylpyrrolidone complexed with hydrogen peroxide.

In some embodiments, the present invention provides oral care compositions comprising from about 1 to about 20% of an additional linear and/or crosslinked polyvinylpyrrolidone. Some embodiments provide compositions comprising from about 1 to about 15%, by weight, of an additional linear and/or crosslinked polyvinylpyrrolidone. Some embodiments provide compositions comprising from about 1 to about 10%, by weight, of an additional linear and/or crosslinked polyvinylpyrrolidone. Some embodiments provide compositions comprising from about 5 to about 15%, by weight, of an additional linear and/or crosslinked polyvinylpyrrolidone. Other embodiments provide compositions comprising from about 7 to about 12%, by weight, of an additional linear and/or crosslinked polyvinylpyrrolidone. Further embodiments provide oral care compositions comprising from about 8 to about 11%, by weight, of an additional linear and/or crosslinked polyvinylpyrrolidone. Still further embodiments provide compositions comprising from about 8.5 to about 10%, by weight, of an additional linear and/or crosslinked polyvinylpyrrolidone. Still other embodiments provide oral care compositions comprising 9.9% or 10%, by weight, of an additional linear and/or crosslinked polyvinylpyrrolidone. Yet other embodiments provide oral care compositions comprising about 9%, by weight, of an additional linear and/or crosslinked polyvinylpyrrolidone.

The amount of pigment in the oral composition is from 0.01 to 3%, more particularly from 0.02 to 1%, and more particularly from 0.01 to 0.08% by weight. The pigment may be uniformly spread throughout the composition or, it may be dispersed in a second phase such as a stripe or other coextruded second phase. Such "dual phase" compositions have the advantage that the phases may be differently colored, presenting a more visually attractive product to the consumer.

In some embodiment the pigment is violet or blue, preferably one of those listed in the Colour Index International. These pigments are listed as pigment violet 1 through to pigment violet 56 and pigment blue 1 through 83. Examples of pigment violets are pigment violet 1, 1:1, 1:2, 2, 3, 5:1, 13, 19, 23, 25, 27, 31, 32, 37, 39, 42, 44 and 50. Examples of pigment blues are pigment blue 1, 2, 9, 10, 14, 15, 15:1, 15:2, 15:3, 15:4, 15:6 16, 18, 19, 24:1, 25, 56, 60, 61, 62 and 66. Other suitable pigments are pigment ultramarine blue and ultramarine violet. The pigment should have a hue angle, h, in the CIELAB system of from 200 to 320 degrees more particularly between 250 and 290 degrees. A detailed description of hue angle may be found on p 57 of Colour Chemistry 3rd edition by H. Zollinger published by Wiley-VCH. While the preferred single pigments are blue or violet, the same effect may be achieved through mixing pigments outside of this h range; for example, such a hue angle may also be obtained by mixing a red and blue pigment to yield a blue or blue-violet shaded pigment. Typically, the pigment is Pigment Blue 15, more specifically Pigment Blue 15:1, 15:2, 15:3, 15:4, 15:5 or 15:6. Typically, the pigment is capable of reflecting sufficient light such that the treated tooth is perceivably whiter than its initial color. Preferably, the pigment is colored such that its natural color is within the violet-red to green-blue color, typically from violet to blue. If a red pigment is used, the red pigment is typically present in a weight ratio of red pigment to blue pigment of about 0.1:1 to about 1:1. The red pigment used should be stable in a peroxide composition.

A pigment is generally understood to be a shade/material which is insoluble in the relevant medium, at the relevant temperature. This is in contrast to dyes which are soluble. In the context of this invention, the "relevant medium" is human saliva, the liquid medium in which the composition is used, at the temperature of the oral cavity during brushing of the teeth, i.e. up to 37° C. As a reasonable approximation, the relevant medium may be considered to be water and the relevant temperature to be 25° C.

In addition to the pigment and $PVP/H_2O_2$ complex, the compositions of the invention comprise an orally acceptable carrier, which includes all ingredients other than the pigment and $PVP/H_2O_2$ complex.

Some embodiments of the present invention provide a toothpaste or gel-based peroxide compositions further comprise a calcium abrasive. In some embodiments, the compositions comprise from about 9 to about 25%, by weight, propylene glycol. In some embodiments, the compositions comprise from about 14 to about 32%, by weight, glycerin. In other embodiments, the compositions comprise less than 20%, by weight, of a calcium abrasive. Some embodiments provide compositions comprising from about 9 to about 25%, by weight, propylene glycol; from about 14 to about 32%, by weight, glycerin; and about 5 to about 30%, by weight, of a calcium abrasive.

Still other embodiments provide oral care compositions comprising from about 20 to about 60%, by weight, humectant.

Yet further embodiments provide oral care compositions comprising from about 5 to about 60%, or 5 to 30%, or 5 to 25%, or 10 to 25% by weight, abrasive.

The compositions of the invention a "low water" content, meaning that a total concentration of water, including any free water and all water contained in any ingredients, is less than about 5%, preferably less than 3%, preferably less than 2% water.

Where abrasives are present, the average particle size is generally about 0.1 to about 30 microns, for example about 1 to about 20 or about 5 to about 15 microns.

In various embodiments of the present invention, the oral composition comprises an anticalculus (tartar control) agent. Generally, tartar control agents are categorized as being incompatible with some whitening agents, but embodiments of the present invention incorporate tartar control agents and whitening agents in a single phase whitening composition. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. In some embodiments the anticalculus agent is present at about 0.1% to about 30%. The oral composition may include a mixture of different anticalculus agents. In one preferred embodiment, tetrasodium pyrophosphate (TSPP) and/or sodium acid pyrophosphate (SAPP) are used. In the one embodiment, the anticalculus agent comprises TSPP at about 1-2% and/or SAPP at about 0.5 to 5%. In another embodiment, tetrasodium pyrophosphate (TSPP) and/or sodium tripolyphosphate (STPP) are used. In one preferred embodiment, the anticalculus agent comprises TSPP at about 1-2% and/or SAPP at about 0.01% to 10%, or 0.01 to 5%, or 0.1 to 5%, or 0.1 to 4%, or 1 to 10%.

The oral care composition can optionally include at least one orally acceptable source of fluoride ions. Any known or to be developed in the art may be used. Suitable sources of fluoride ions include fluoride, monofluorophosphate and fluorosilicate salts. Specific examples include stannous fluoride, sodium fluoride, potassium fluoride, sodium monofluorophosphate, sodium fluorosilicate, ammonium fluorosilicate, amine fluoride, ammonium fluoride, and combinations thereof. One or more fluoride ion-releasing compound is optionally present in an amount providing a total of about 100 to about 20,000 ppm, about 200 to about 5,000 ppm, or about 500 to about 2,500 ppm, fluoride ions. Fluoride ion sources may be added to the compositions of the invention at a level of about 0.01 wt % to about 10 wt % in one embodiment or about 0.03 wt % to about 5 wt. %, in another embodiment about 0.1 to about 2 wt %, in another embodiment about 0.1 to about 1.5 wt %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

The compositions of the invention may also comprise various dentifrice ingredients to adjust the rheology and feel of the composition such as humectants, surface active agents, thickening or gelling agents, etc.

The compositions of the present invention may comprise a surface active agent (surfactant). Suitable surfactants include without limitation water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine.

The compositions of the present invention optionally comprise a thickener. Any orally acceptable thickening agent can be used, including without limitation carbomers, also known as carboxyvinyl polymers, carrageenans, also known as Irish moss and more particularly—carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, and colloidal and/or fumed silica and mixtures of the same. One or more thickening agents are optionally present in a total amount of about 0.1% to about 90%, for example about 1% to about 50% or about 5% to about 35%.

In various preferred embodiments, the compositions may comprise polymers and/or copolymers of polyethylene glycol, of ethylene oxide/propylene oxide, and of silicone. If such copolymers/polymers are used, they may be selected from commercially available materials. In one embodiment such block copolymer is an ethylene oxide, propylene oxide block co-polymer of formula (ethylene oxide)$_x$-(propylene oxide)$_y$, wherein x is an integer of 80-150, e.g. 100-130, e.g. about 118, and y is an integer 30-80, e.g. about 60-70, e.g. about 66, having an average molecular weight of greater than 5000, e.g., 8000-13000 Da, e.g. about 9800. Block copolymers of ethylene oxide/propylene oxide are useful, but higher molecular weight, e.g., >5000 Da are preferred, e.g. including PLURACARE® L1220 (available from BASF, Wyandotte, Mich., United States of America). Low or medium molecular weight polyethylene glycol, e.g., PEG 400, PEG 600, PEG 800, PEG 1000 and mixtures thereof are also useful.

It is preferred that the carrier(s) provide a dentifrice with a viscosity of about 10,000 CPS to about 700,000 CPS, preferably about 30,000 CPS to about 300,000 CPS.

As recognized by one of skill in the art, the oral compositions of the present invention optionally include other materials, such as for example, anti-caries agents, desensitizing agents, viscosity modifiers, diluents, surface active agents, such as surfactants, emulsifiers, and foam modulators, pH modifying agents, abrasives, in addition to those listed above, humectants, mouth feel agents, sweetening agents, flavor agents, colorants, preservatives, and combinations thereof. It is understood that while general attributes of each of the above categories of materials may differ, there may be some common attributes and any given material may serve multiple purposes within two or more of such categories of materials. Preferably, the carrier is selected for compatibility with other ingredients of the composition.

Flavorants, sweeteners, colorants, foam modulators, mouth-feel agents and others additively may be included if desired, in the composition.

The compositions of the present invention optionally comprise one or more further active material(s), which is operable for the prevention or treatment of a condition or disorder of hard or soft tissue of the oral cavity, the prevention or treatment of a physiological disorder or condition, or to provide a cosmetic benefit.

The compositions may include a stannous ion or a stannous ion source. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%.

The compositions of the present invention optionally comprise an antimicrobial (e.g., antibacterial) agent. A further illustrative list of useful antibacterial agents is provided in such as those listed in U.S. Pat. No. 5,776,435 to Gaffar et al., the contents of which are incorporated herein by reference. One or more antimicrobial agents are optionally present in an antimicrobial effective total amount, typically about 0.05% to about 10%, for example about 0.1% to about 3%.

The compositions of the present invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the present invention optionally comprise a sialagogue or saliva-stimulating agent, an anti-plaque agent, an anti-inflammatory agent, and/or a desensitizing agent.

pH modifying agents among those useful herein include acidifying agents to lower pH, basifying agents to raise pH, and buffering agents to control pH within a desired range. For example, one or more compounds selected from acidifying, basifying and buffering agents can be included to provide a pH of 2 to 10, or in various embodiments from 2 to 8, from 3 to 9, from 4 to 8, from 5 to 7, from 6 to 10, and from 7 to 9. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range.

While ingredients are sometimes identified herein by category, e.g., humectant, antioxidant, thickener, etc., this identification is for convenience and clarity, but is not intended to be limiting. All of the ingredients in the compositions may have functions in addition to their primary function, and may contribute to the overall properties of the composition, including its stability, efficacy, consistency, mouthfeel, taste, odor and so forth.

The product form of the compositions of the invention can be a dentifrice, mouthrinse, strip, or gel. The term "dentifrice" generally denotes formulations which are used to clean the surfaces of the oral cavity. The dentifrice is an oral composition that is not intentionally swallowed for purposes of systemic administration of therapeutic agents, but is applied to the oral cavity, used to treat the oral cavity and then expectorated. Typically the dentifrice is used in conjunction with a cleaning implement such as a toothbrush, usually by applying it to the bristles of the toothbrush and then brushing the accessible surfaces of the oral cavity. Preferably the dentifrice is in the form of a paste or a gel (or a combination thereof).

Methods are provided to whiten a tooth surface in a human or animal subject comprising contacting a composition of the invention, e.g., Composition 1, et seq. as described above, and with the tooth surface. In one embodiment the composition remains stable when stored for at least 1 week, at least 2 weeks, at least 1 month, at least 3 months, at least 6 months, or at least 1 year prior to contacting with the tooth surface. In one embodiment the composition is stored at room temperature. As used herein "animal subject" includes higher order non-human mammals such as canines, felines, and horses. The oral care composition is contacted with an oral surface of the mammalian subject to thereby whiten teeth in a highly efficacious manner, without any negative interaction between the whitening agent, the blue to blue-violet pigment, and other ingredients.

In various embodiments, it is preferred that the oral care composition is applied and contacted with the oral surface. The dentifrice, prepared in accordance with the present invention is preferably applied regularly to an oral surface, preferably on a daily basis, at least one time daily for multiple days, but alternately every second or third day. Preferably the oral composition is applied to the oral surfaces from 1 to 3 times daily, for at least 2 weeks up to 8 weeks, from four months to three years, or more up to lifetime.

The compositions of the invention can be packaged into containers or dispensers known in the art, via means conventional in the art. In some embodiments the compositions are packaged into tubes, metal, plastic or laminated, with either screw top or flip top caps.

In some embodiments, the diameter of the top of the tube in which the a composition of the present invention is packaged, expands less than 0.1 cm, after 1 week of aging at 60° C. While in other embodiments, the diameter of the top of the tube in which a composition of the present invention is packaged, does not expand to a measurable extent.

In some embodiments, the compositions of the present invention do not exhibit an unacceptable level of phase separation, e.g., after 30 minutes at 2050 rpm in a LumiSizer 110 analytical centrifuge.

The invention is illustrated in the following non-limiting examples.

Examples

Comparison of Various Compositions
The formulations are generally described in Table 1

TABLE 1

| Formulations | Description |
| --- | --- |
| A | Peroxide and pigment |
| B | Peroxide and dye |
| C | Peroxide and no colorant |
| D | No peroxide, only pigment |

The formulation ingredients are shown in Table 2

TABLE 2

| | Formula | | | |
| --- | --- | --- | --- | --- |
| Ingredient | A | B | C | D |
| BHT | 0.03 | 0.03 | 0.03 | |
| Calcium pyrophosphate | 20 | 20 | 20 | |
| cellulose gum | | | | X |
| Pigment Blue 15 | 0.075 | — | — | X |
| Blue Dye | | 0.075 | | |
| Titanium Dioxide | | | | X |
| Crosslinked PVP | 5.75 | 5.75 | 5.75 | |
| Flavor | 1.4 | 1.4 | 1.4 | |
| Fluoride | 1.1 | 1.1 | 1.1 | X |
| Fumed Silica | 1.75 | 1.75 | 1.75 | |
| Glycerin | 36.34 | 36.34 | 36.34 | X |
| hydrated silica | | | | X |
| L1220 | 7.5 | 7.5 | 7.5 | |

TABLE 2-continued

| Ingredient | Formula | | | |
|---|---|---|---|---|
| | A | B | C | D |
| lecithin | | | | X |
| limonene | | | | X |
| mica | | | | X |
| PEG 600 | 6.31 | 6.31 | 6.31 | |
| PEG-323 | | | | X |
| PG | 15 | 15 | 15 | |
| Phosphoric Acid | 0.2 | 0.2 | 0.2 | |
| PVM/MA copolymer | | | | X |
| PVP. HP | 0.55 | 0.55 | 0.55 | |
| Sodium lauryl sulfate | 2 | 2 | 2 | X |
| sodium saccharin | | | | X |
| sorbitol | | | | X |
| Tetrasodium Pyrophosphate | 2 | 2 | 2 | |
| trisodium phosphate | | | | X |
| Water | 0 | 0 | 0 | X |

Color Stability Measuring Procedure:

Calibrate the colorimeter. Add toothpaste samples of Formulations A-D to an appropriate cuvette. Measure the color to obtain the baseline measurements Add aged (1 week in 60° C.) sample formulations to a cuvette and measure color. Add aged (2 week in 60° C.) sample formulations to a cuvette and measure the color. Evaluate change in L* (L* of 100=lightest, L*=0 is darkest). Compare sample final change in L*.

In-Vitro Brushing Procedure

Prophy artificially stained bovine enamel to achieve similar initial lightness values. Mount bovine teeth into a tray. Prepare 1:1 (w/w) slurry of dentifrice to DI water and add 25 grams to brushing tray. Brush the stained bovine teeth for 2 minutes at 120 strokes/min. Rinse teeth with 100 ml DI water then evaluate teeth for L*,a*,b* values with spectrophotometer ("in vitro brushing"). The teeth are then soaked in DI water for 1 hr with agitation and then evaluated for L*,a*,b* values with spectrophotometer to measure the amount of blue retained ("in vitro retention").

Spectrophotometer Metrics

CIELAB color scale is used.

b* value: +b*=yellow and −b*=blue

ΔWIO—Optimized version of the CIE whiteness index

Two toothpaste formulas, one containing peroxide and Pigment Blue 15 and another containing peroxide and blue dye (FD&C blue #1), are aged for two weeks in a 60° C. oven and the peroxide stability is analysed. Table 3 shows the analytical results of aged low peroxide toothpaste with pigment blue vs a low peroxide with blue dye showing degradation of peroxide. The results from Table 3 indicate a significant loss of peroxide active in toothpaste containing blue dye as compared to dentifrice containing Pigment blue.

Table 3 shows the in-vitro brushing results of low peroxide toothpaste with pigment blue vs. a commercial instant whitening toothpaste. The results from Table 3 indicate the low peroxide formula with pigment blue provides more whitening and change of blue on the tooth surface than a commercial instant whitening product after only one application of the product.

Table 3 shows the in-vitro retention results of low peroxide toothpaste with pigment blue vs. a commercial instant whitening toothpaste. The results indicate the product containing low peroxide and pigment blue is better at retaining blue on the surface of teeth than a commercial instant whitening product.

Table 4 shows the in-vitro brushing results of low peroxide toothpaste with pigment blue vs. a toothpaste without colorant. The results indicate the product containing low peroxide and pigment blue is more whitening and change of blue on the tooth surface than the product without pigment after only one application of the product.

TABLE 3

| Formulation | Initial Oxygen | 1 week 60 C. Oxygen | 2 week 60 C. Oxygen | Initial Δb* | 1 week 60 C. Δb* | ΔWIO, in vitro brushing | Δb*, in vitro brushing | ΔWIO, in vitro retention | Δb*, in vitro retention |
|---|---|---|---|---|---|---|---|---|---|
| A | 0.11 | 0.1 | 0.09 | 35.59 | 33.91 | 6.2 | −1.9 | 2.8 | −0.5 |
| B | 0.12 | 0.07 | 0.05 | 34.41 | 4.33 | — | — | — | — |
| D | — | — | — | — | — | 3.2 | −1.4 | −1 | 0 |

TABLE 4

| Formulation | ΔWIO, in vitro brushing | Δb*, in vitro brushing |
|---|---|---|
| A | 11.8 | −1.7 |
| C | 8.9 | −1 |

What is claimed is:

1. A dentifrice composition comprising (i) a whitening complex comprising crosslinked polyvinylpyrrolidone complexed with hydrogen peroxide, and (ii) a pigment having a blue to blue-violet color with a hue angle in the CIELAB system ranging from 200 to 320 degrees.

2. The composition of claim 1 further comprising an ethylene oxide, propylene oxide block co-polymer of average molecular weight greater than 5000 Da.

3. The composition of claim 2 wherein the ethylene oxide, propylene oxide block co-polymer comprises (ethylene oxide)$_x$-(propylene oxide)$_y$, wherein x is an integer of 80-150 and y is an integer 30-80.

4. The composition of claim 1 wherein the whitening complex contains about 10-30% hydrogen peroxide, by weight, and about 5-15% total nitrogen by weight.

5. The composition of claim 1 wherein the total amount of hydrogen peroxide by weight of the composition is about 0.05 to 4% by weight.

6. The composition of claim 1 wherein the amount of pigment is about 0.01 to 3% by weight.

7. The composition of claim 1 wherein the pigment has a hue angle in the CIELAB system ranging from 250 to 290 degrees.

8. The composition of claim 1 additionally comprising polyethylene glycol of average molecular weight 400 to 800 Da.

9. The composition of claim 1 which contains less than 3% water.

10. The composition of claim 1 which is a toothpaste comprising a calcium abrasive selected from a calcium phosphate salt, calcium carbonate, or calcium pyrophosphate.

11. The composition of claim 1 further comprising tetrasodium pyrophosphate.

12. The composition of claim 1 comprising the following ingredients by weight:

| | |
|---|---|
| Glycerin | 10-60 wt % |
| Propylene glycol | 0.01-60 wt % |
| Ethylene oxide, propylene oxide block co-polymer, avg. MW >5 kDa | 0.01-15% |
| Crosslinked polyvinylpyrrolidone complexed with 15-25% hydrogen peroxide | 0.05-25 wt % |
| Pigment having a hue angle in the CIELAB system ranging from 250 to 290 degrees. | 0.02-1 wt % |
| Calcium pyrophosphate | 0.01-45 wt % |
| TSPP and/or SAPP | 0.01-5 wt %. |

13. The composition of claim 1 comprising additional linear and/or crosslinked polyvinylpyrrolidone.

14. The composition of claim 12 comprising:

| | |
|---|---|
| Glycerin | 20-50 wt % |
| Propylene glycol | 5-25 wt % |
| Ethylene oxide, propylene oxide block co-polymer, avg. MW >5 kDa | 5-12% |
| Additional linear and/or crosslinked polyvinylpyrrolidone | 1-10 wt % |
| Crosslinked polyvinylpyrrolidone complexed with 15-25% hydrogen peroxide | 0.25-10 wt % |
| Pigment having a hue angle in the CIELAB system ranging from 250 to 290 degrees. | 0.01-0.08 wt % |
| Calcium pyrophosphate | 5-30 wt % |
| TSPP and/or SAPP | 0.1-5 wt %. |

15. A method for whitening a tooth surface in a human or animal subject comprising contacting a composition of claim 1 with the tooth surface.

* * * * *